US00PP09891P

United States Patent [19]

Glicenstein

[11] Patent Number: Plant 9,891

[45] Date of Patent: May 13, 1997

[54] CHRYSANTHEMUM PLANT NAMED 'BOLD CHRISTINE'

[75] Inventor: Leon Glicenstein, Salinas, Calif.

[73] Assignee: Yoder Brothers, Inc., Barberton, Ohio

[21] Appl. No.: 605,820

[22] Filed: Feb. 22, 1996

[51] Int. Cl.[6] ..... A01H 5/00

[52] U.S. Cl. ..... Plt./82

[58] Field of Search ..... Plt./76, 81, 82

[56] References Cited

U.S. PATENT DOCUMENTS

| | | | |
|---|---|---|---|
| P.P. 8,988 | 11/1994 | Vanden Berg | Plt./81 |
| 4,616,099 | 10/1986 | Sparkes | 47/58 |

OTHER PUBLICATIONS

Broertjes, et al., 1980, "A Mutant of a Mutant of a . . . Irradiation of Progressive Radiation–Induced Mutants in a Mutation Breeding Programme with *Chrysanthemum morifolium*," Euphytica, 29:525–530.

Gosling, ed., 1979,"The Chrysanthemum Manual–6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci Pub. Co., New York, pp. 162–175.

Searle, et al., 1968, "Chrysanthemums the Year Round", Blanford Press, London, pp. 27–29, 320–327.

Chan, 1966, "Chrysanthemum and Rose Mutations Induced by X–rays", Am. Soc. Hart. Sci. Proc., pp. 613–620.

Broertjes, 1966, "Mutation Breeding of Chrysanthemums", Euphytica, 15:156–162.

Dowrick, et al., 1966, "The Induction of Mutations in Chrysanthemum using X–and Gamma Radiation", Euphytica, 15:204–210.

*Primary Examiner*—Howard J. Locker
*Attorney, Agent, or Firm*—Foley & Lardner

[57] ABSTRACT

A Chrysanthemum plant named Bold Christine particularly characterized by its flat capitulum form; decorative capitulum type; dark red to greyed-red ray floret color; diameter across face of capitulum of 60 to 64 mm when fully opened; branching pattern is spreading and prolific, with 7 to 9 laterals developing after pinch when grown outside under natural daylength in fall flowerings; natural season flower date of August 24 September 2 when planting rooted cuttings on June 17 to 21 in Salinas, Calif., and of September 23 to October 5 when planting rooted cuttings June 15 to 18 in Hightstown, N.J.; plant height of 36 to 41 cm when grown in fall under natural daylength with no growth regulators; and durable, uniform performance.

1 Drawing Sheet

The present invention comprises a new and distinct cultivar of Chrysanthemum, botanically known as *Dendranthema grandiflora*, and referred to by the cultivar name Bold Christine.

Bold Christine, identified as 7994 (89-755I01), is a product of a mutation induction program. The new cultivar was discovered and selected by inventor Leon Glicenstein on Sep. 1, 1993 in a controlled environment in Salinas, Calif., as one flowering plant within a flowering block established as rooted cuttings from stock plants which had been exposed as unrooted cuttings to an X-ray source of 1750 rads in Fort Myers, Fla. on Feb. 11, 1993 . The irradiated parent cultivar was the cultivar Christine, disclosed in U.S. Plant Pat. No. 8,988 and described as a flat decorative garden mum with coral-red flower color.

The irradiation program resulting in Bold Christine had as its primary objective the expansion of color ranges of the parent cultivar Christine. The irradiation program comprised irradiation of cuttings of the parent cultivar at irradiation levels of 1500, 1750 and 2000 rads. A total of 466 cuttings harvested from a total of 225 irradiated plants were planted on June 21, 1993. Of these, 4 initial selections were made, which selections were then revegetated and reflowered. One selection died during the revegetation process. Three consecutive flowerings resulted in discarding 1 of the original selections on Oct. 17, 1994. The remaining 2 selections were maintained as PIs (Possible Introductions) and further trialed in Salinas, Calif., Hightstown, N.J. and Leamington, Ontario, Canada, ultimately resulting in the decision to introduce one selection as Bold Christine, and the other selection as Blushing Christine, disclosed in pending application Ser. No. 08/605,611.

The first act of asexual reproduction of Bold Christine was accomplished when vegetative cuttings were taken from the initial selection in November of 1993 in a controlled environment in Salinas, Calif., by technicians working under supervision of Leon Glicenstein.

Horticultural examination of controlled flowerings of successive plantings has shown that the unique combination of characteristics as herein disclosed for Bold Christine are firmly fixed and are retained through successive generations of asexual reproduction.

Bold Christine has not been obsered under all possible environmental conditions. The phenotype may vary significantly with variations in environment such as temperature, light intensity and daylength, without, however, and variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October.

The following traits have been repeatedly observed and are determined to be basic characteristics of Bold Christine, which, in combination, distinguish this Chrysanthemum as a new and distinct cultivar:

1. Flat capitulum form.
2. Decorative capitulum type.
3. Dark red to greyed-red ray floret color.
4. Diameter across face of capitulum of 60 to 64 mm when fully opened.

5. Branching pattern is spreading and prolific, with 7 to 9 laterals developing after pinch when grown outside under natural daylength in fall flowerings.

6. Natural season flower date of August 24 to September 2 when planting rooted cuttings on June 17 to 21 in Salinas, Calif., and of September 23 to October 5 when planting rooted cuttings June 15 to 18 in Hightstown, N.J.

7. Plant height of 36 to 41 cm when grown in fall under natural daylength with no growth regulators.

8. Durable, uniform performance.

The accompanying photographic drawing is a color photograph of Bold Christine grown as a pinched garden mum under natural season outside conditions in Salinas, Calif., with the colors being as nearly true as possible with illustrations of this type. Plants were grown outside and dug and transplanted in 15 cm pots for photography purposes.

Of the commerical cultivars known to the inventor, the most similar in comparison to Bold Christine is the parent cultivar Christine. All traits of Bold Christine are similar to those of Christine, except for the ray floret color. The ray floret color of Bold Christine is dark red to greyed-red (R.H.S. between 46A and 180), while the ray floret color of Christine is described as coral-red (R.H.S. 51A to 51B).

In the following description color references are made to the Royal Horticultural Society Colour Chart. The Color values were determined on plant material grown as a pinched garden mum grown outdoors in Salinas, Calif. on Sep. 1, 1995.

Classification:

*Botanical.—Dendranthema grandiflora* cv Bold Christine.

*Commercial.*—Flat decorative garden mum.

INFLORESCENCE

A. Capitulum:

*Form.*—Flat

*Type.*—Decorative.

*Diameter across face.*—60 to 64 mm when fully opened.

B. Corolla of ray florets:

*Color (general tonality from a distance of three meters)* .—Dark red to greyed-red.

*Color (upper surface).*—Between 46A and 180A.

*Color (under surface).*—180A to 180B.

*Shape.*—Cross-section flat, longitudinal section straight. Ray floret tips rounded.

C. Corolla of disc florets

*Color (mature).*—14A.

*Color (immature).*—14A, tinged with 144C.

D. Reprodutive organs

*Androecium.—Present on disc florets only; scant pollen.*

*Gynoecium.—Present on both ray and disc florets.*

PLANT

A. General Appearance:

Height.—36 to 41 cm when grown in fall under natural daylength with no growth regulators.

Branching pattern.—Spreading and prolific, with 7 9 laterals developing after pinch when grown outside under natural daylength in fall flowerings.

B. Foliage:

*Color (upper surface).*—147A.

*Color (under surface).*—147B.

*Shape.—Small, lobed, moderately serrated.*

What is claimed is:

1. A new and distinct Chrysanthemum plant named Bold Christine, as described and illustrated.

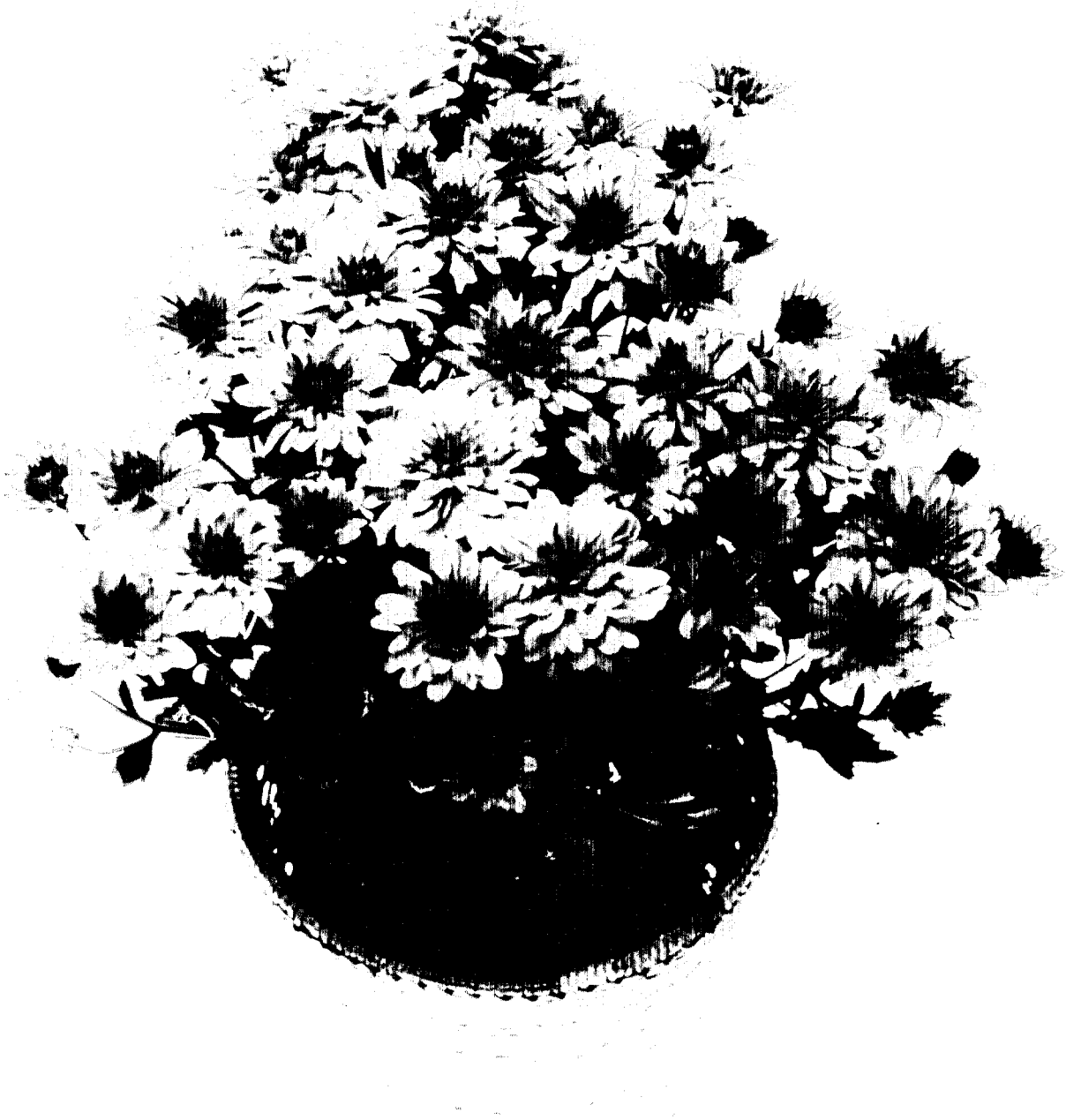

* * * * *